United States Patent [19]

Ajani et al.

[11] Patent Number: 4,859,452
[45] Date of Patent: Aug. 22, 1989

[54] METHODS FOR THE REDUCTION OF DIFLUOROMETHYLORNITHINE ASSOCIATED TOXICITY

[75] Inventors: Jaffer Ajani; Bruce Grossie, Jr.; Kenji Nishioka; David M. Ota, all of Houston, Tex.

[73] Assignee: Board of Regents, The University of Texas System, Austin, Tex.

[21] Appl. No.: 2,890

[22] Filed: Jan. 13, 1987

Related U.S. Application Data

[63] Continuation-in-part of Ser. No. 820,517, Jan. 17, 1986.

[51] Int. Cl.$^4$ ............................................... A61K 00/00
[52] U.S. Cl. ...................................... 424/10; 514/922
[58] Field of Search ............................ 514/922; 424/10

[56] References Cited

U.S. PATENT DOCUMENTS

| | | | |
|---|---|---|---|
| 3,235,597 | 2/1966 | Mills | 260/570.5 |
| 3,236,601 | 2/1966 | Harvill | 23/230 |
| 3,764,703 | 10/1973 | Bergstrom | 424/319 |
| 3,832,465 | 8/1974 | Ghadimi | 424/177 |
| 3,950,529 | 4/1976 | Fischer et al. | 424/273 |
| 4,065,552 | 12/1977 | Costa | 424/1 |
| 4,444,890 | 4/1984 | Burzynski | 436/64 |
| 4,542,750 | 9/1985 | Ettare | 128/760 |

OTHER PUBLICATIONS

Dredsson et al, "Reversal of the Growth Inhibitory Effect of Alpha-Difluoromethylornithine by Putrescine But Not by Other Divalent Cations", Mol. Cell. Biochem 64(2) pp. 163-172 (1984).
Ota et al. (1984) *Jrnl Clin Oncol.*, 2:1157.
Ota et al. (Abstract #16) and Grossie et al. (Abstract #71), Aspen Abstracts (1985).
Progress in Cancer Research and Therapy, Raven Press, N.Y. (1978).
Grossie et al. (1986), *Cancer Res.*, 46:3464-3468.
Ota et al. (1986), *Int. J. Cancer*, 38:245-249.

*Primary Examiner*—Douglas W. Robinson
*Assistant Examiner*—Richard Kearse
*Attorney, Agent, or Firm*—Arnold, White & Durkee

[57] ABSTRACT

Disclosed are total parenteral nutrition formulations which include essential amino acids in combination with either arginine or ornithine, for use in the detection of recurrent malignant disease in patients. Such formulations stimulate tumor-specific polyamine production to a greater extent than non-tumor related polyamine production. Additionally, such formulations were found to specifically promote an increase in red blood cell putrescine levels of tumor-bearing rats. Nontumor-bearing rats were not found to be similarly reactive to these formulations. Methods for making and administering these formulations as well as their use in preventing DFMO-induced toxicity are also disclosed.

9 Claims, 2 Drawing Sheets

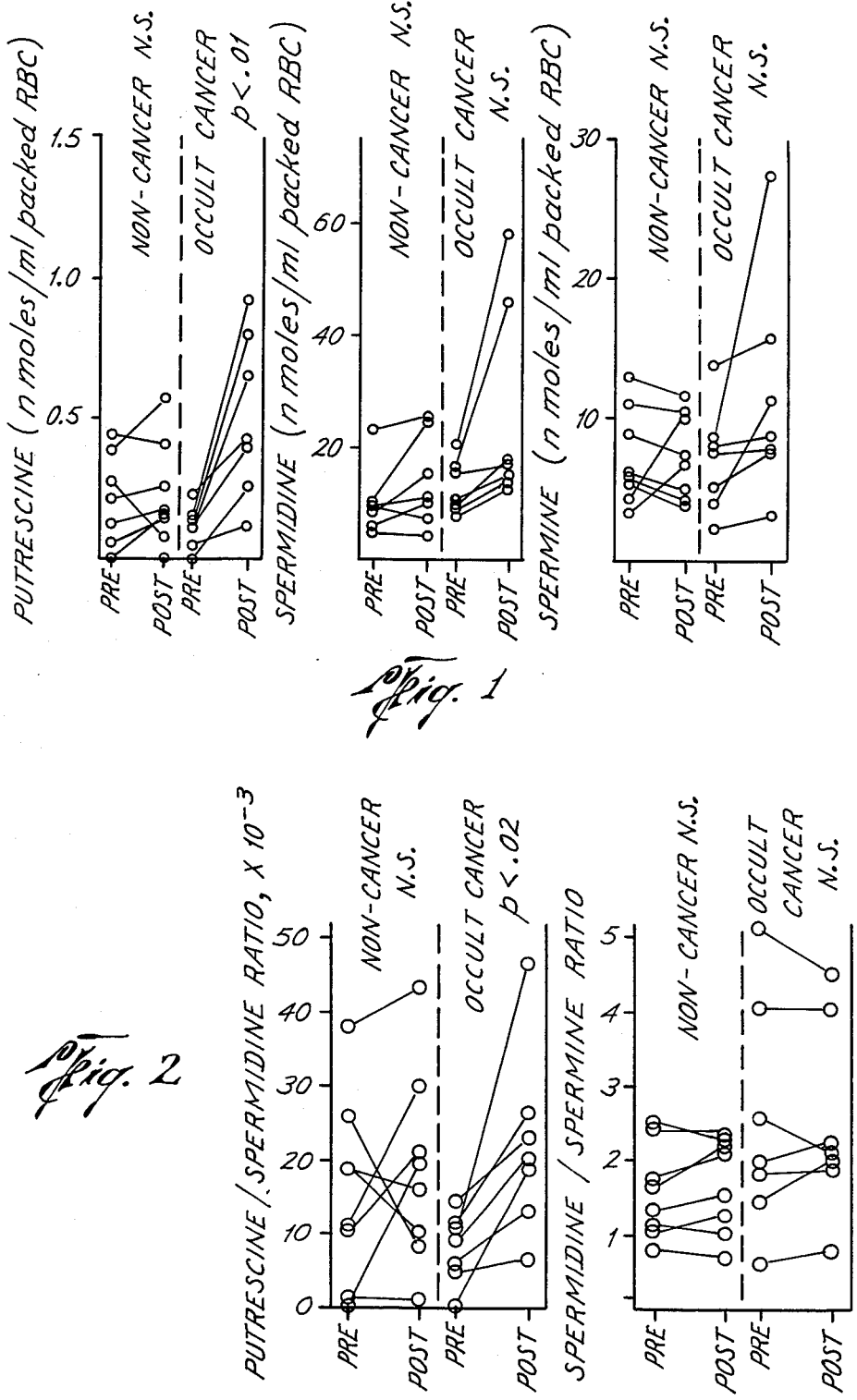

METHODS FOR THE REDUCTION OF DIFLUOROMETHYLORNITHINE ASSOCIATED TOXICITY

The government may own certain rights in the present invention pursuant to NCI grant ROI CA34465.

BACKGROUND OF THE INVENTION

The present application is a continuation-in-part of Ser. No. 820,517, filed Jan. 17, 1986.

1. FIELD OF THE INVENTION

The present invention relates to improved formulations and methods for the detection of malignant disease in a patient. More particularly, the present invention is directed to formulations which augment tumor-related increases in a patient's polyamine level and which additionally prevent drug related side effects in patients undergoing ornithine decarboxylase inhibitor therapy.

2. DESCRIPTION OF THE RELEVANT ART

Polyamines are important in the regulation of protein, RNA and DNA synthesis in mammalian systems and are essential for cell proliferation. The increased excretion of polyamines in the urine of patients with cancer was reported by Russell, D. H. (1971), *Nature*, 233: 144-145. Based on animal studies of tumor growth and regression, spontaneously and in response to radiation and chemotherapy, a model was proposed by Russel et al. (1975), Lancet, 2: 797-799, to summarize the potential role of polyamines as biochemical markers of human tumor cell growth and death. Such observations raised the possibility that measurement of polyamine levels in clinical fluids and tissue specimens could be useful in the diagnosis and evaluation of patients with cancer. For a review of the diagnostic role of polyamines in cancer see "Polyamines and the Clinical Evaluation of Patients with Cancer," Chapter 10, in *Progress in Cancer Research and Therapy*, Raven Press, N.Y., 1978.

Although polyamine measurements in the urine, plasma, and whole blood of patients initially held promise as tumor markers, their use for detecting recurrent systemic disease has been limited. This unreliability is due to both low clinical sensitivity (high number of false negatives) and specificity (high number of false positives). Despite numerous reports of elevated polyamines in patients with malignant disease, overlapping standard deviations of polyamine levels between cancer and noncancer patients reduce their sensitivity to accurately detect malignant disease at an early stage. Furthermore, increased polyamine levels have been associated with nonmalignant disease states such as certain inflammatory and infectious diseases. Such unreliability could be removed by the availability of techniques for specifically increasing polyamine levels observed in cancer victims to a level higher than observed in false positives such as infectious disease patients.

Accordingly, techniques for improving the sensitivity and specificity of the polyamine level test as an indicator of malignant disease in man would represent a significant advance in medical science.

SUMMARY OF THE INVENTION

It is an object of the present invention to provide an amino acid formulation for improving the diagnostic reliability of polyamine level determinations as indicators of malignant disease in man. In particular, amino acid formulations prepared in accordance with the present invention and administered to patients promote a specific elevation in the polyamine level of patients with primary or recurrent malignant disease. The term amino acid, as used herein, is defined to include all amino acid-derived compounds which will effectively provide the free 1-amino acid at the intracellular level. For example, peptides are amino acid-derived compounds that when acted upon by metabolic enzymes will provide the free amino acid. Similarly, amino acid derivatives, for example, n-acetylated amino acids, are included within the meaning of the term amino acid.

Formulations include a pharmacologically acceptable amount of a polyamine precursor in combination with at least one of the amino acids, preferably one of the essential amino acids. Essential amino acids as used herein refer to those found by William Rose and his associates to be essential in that they are not normally metabolically produced by the human body. For example, see Rose (1949) *Fed. Proc.*, 8:546 and Rose et al. (1955) *J. Biol. Chem.*, 217:987. Additionally, as used herein polyamine precursors are defined as those amino acids in the metabolic pathway of polyamine production and include methionine, arginine and ornithine.

Such formulations may include any non-toxic amount of each of the included amino acids. Therefore, for the purposes of the present invention, a pharmacologically acceptable amount of an included amino acid generally means any level of that amino acid which is at least high enough to supply minimal metabolically sufficient concentrations of that amino acid to the target cells. However, such formulations could presumably incorporate amino acid concentrations which approach toxicity-inducing levels, for example, in an attempt to "tailor" formulations to fit a particular patient population. In a preferred embodiment, the concentration of included amino acids found to promote good polyamine responses exhibited a range of from 50 to 200 milligrams for tryptophan to 250 to 1400 milligrams for leucine in every 100 milliliters of a parenteral formulation. The preferred range for arginine, ornithine or methionine, the polyamine precursors, is between 50 and 750 mg/100 ml. of solution, however, higher concentrations may be employed where desired. In a more preferred embodiment the concentration of polyamine precursor is approximately 30 mM (which, for example, corresponds to 450 mg ornithine/100 ml. of the formulation).

In another embodiment, the amino acid formulation is conveniently supplied by combining pharmacologically acceptable amounts of ornithine or arginine with commercially available parenteral feeding solutions. Such feeder solutions could prove useful both as parenteral solutions tailored to maximize the sensitivity of detection of recurrent malignant disease and as adjuvants to the cancer-screening of patients who are undergoing parentered feeding.

It is a further object of the present invention to provide methods for detecting cancer in a patient which generally includes administering to the patient one of the parenteral amino acid formulations described and detecting an increase in the patient's polyamine level following administration of the formulation, a relative increase being indicative of cancer in the patient. Relative increase in polyamine levels is meant to include either relative increases with respect to the cancer patient's own pre-administration level or with respect to "normal" patient population's average pre- or post administration polyamine levels.

Although the full advantages of the present invention are particularly exemplified through detection of a relative increase in putrescine, measurement of all of the polyamines, including spermadine, spermine and putrescine, is sufficient for most uses.

Similarly, although polyamine levels may be determined in any of a number of patient samples, including cerebrospinal fluid, urine, plasma, serum and whole blood, in a preferred embodiment, the patient's red blood cell (RBC) polyamine levels are measured as a more sensitive indicator of polyamine levels.

It is still a further object of the present invention to provide formulations for use in preventing or reducing the occurrence of ODC-related toxicities in patient's undergoing OCD therapy. In this regard, it is demonstrated herein that amino acid formulations which are formulated to include a polyamine precursor, preferably ornithine, can reduce or reverse DFMO induced thrombocytopenia. Moreover, it has been found that for such uses, polyamine precursors may be administered either alone or in combination with other amino acids.

BRIEF DESCRIPTION OF THE DRAWINGS

FIG. 1. Graphs demonstrate changes in RBC putrescine, spermidine, and spermine levels in noncancer patients and patients with clinically occult malignant disease during TPB (total parentenal nutrition) therapy. PRE indicates RBC polyamine levels before preoperative TPN was started, and POST indicates levels after 7-10 days of preoperative TPN but before surgery. N.S. indicates not significant.

FIG. 2. Graphs demonstrate changes in RBC putrescine: spermidine and spermidine: spermine ratios in noncancer patients and patients with clinically occult malignant disease during TPN. PRE indicates RBC polyamine ratios before preoperative TPN was started and POST indicate ratios after 7-10 days of preoperative TPN but before surgery. N.S. indicates not significant.

DETAILED DESCRIPTION OF THE PREFERRED EMBODIMENTS

Figure 3:
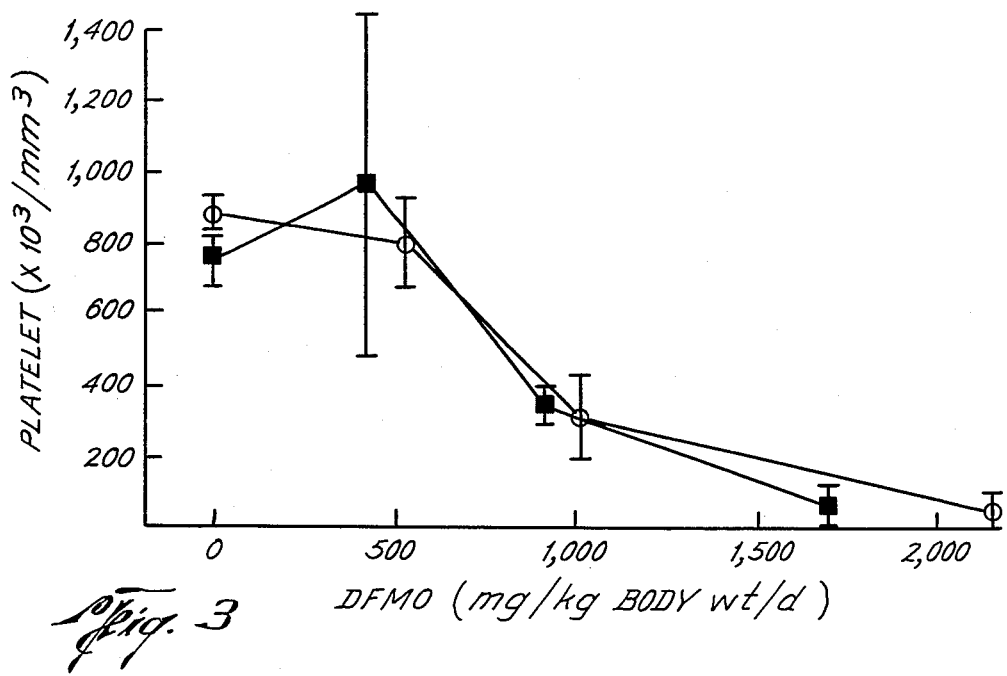
FIG. 3. Platelet counts plotted against dose of DFMO given as a continuous i.v. infusion for 12 days in tumor-bearing ( ) and nontumor-bearing rats ( ). Bars indicate standard deviation. As the dose of DFMO increases, there is significant platelet suppression. This experiment was done to determine if simultaeous ornithine infusion could block platelet suppression.

The present invention, in its most general and overall scope, is directed to amino acid formulations, including amino acid formulations which contain the amino acid ornithine, methionine or arginine, useful in the stimulation of polyamine formation in the tumor-bearing individual. Methods are provided which utilize these amino acid formulations to improve the diagnostic reliability of polyamine level determination in cancer screening and cancer staging. Additionally, such formulations provide the capability of reducing toxicities associated with anti-tumor chemotherapy aimed at blocking polyamine production.

a. Introduction

Polyamine production is associated with cell division. Increases in the intracellular levels of polyamines, particularly putrescine and spermidine, in the early phase of both normal and neoplastic cell proliferation are well documented. Conversely, a reduction in tumor burden is associated with a reduction of polyamine levels suggesting the potential use of polyamines as a biological marker of tumor growth. A substantial portion of circulating polyamines are carried in the RBC. Because the enzyme systems necessary to synthesize polyamines are not found in enucleated RBC, it is theorized that RBC are carriers of polyamines from sites of production to sites of conjugation and excretion.

The pathway for polyamine synthesis begins with Lornithine. This natural amino acid, although not normally incorporated into proteins, is part of the urea cycle which metabolizes arginine to ornithine and ureas. Ornithine is converted by ornithine decarboxylase (ODC) to putrescine and $CO_2$, the rate-limiting step in the production of polyamines. Putrescine is converted to spermidine by spermidine synthetase in association with the decarboxylation of S-adenosylmethionine by S-adenosylmethionine decarboxylase. Spermidine is then converted to spermine by spermine synthetase, again in association with the decarboxylation of S-adenosylmethionine. Putrescine, spermidine and spermine represent the three primary polyamines.

It has been found that infusion of feeding solutions which contain precursors of polyamine metabolism, alter polyamine metabolism in the tumor-bearing host. One example is parenteral nutrition formulations which contain methionine, arginine and/or ornithine. Total parenteral nutrition formulations (TPM) are specific feeding solutions which generally contain higher amino acid concentrations that supplementary feeding solutions, for example. TPN is a technique used to intravenously feed malnourished cancer patients. These nutrient solutions generally contain concentrated glucose, crystalline amino acids, electrolytes and vitamins. The amino acid compositions of typical commercially available amino acid solutions are shown below in Table 1. Each amino acid is purchased in crystalline form and compounded into amino acid solutions. Unique amino acid solutions are marketed for patients with kidney failure, liver failure and trauma patients. No special solutions exist for cancer patients for lack of specific needs or rationale.

TABLE I

AMINO ACID COMPARISON
REPRESENTATIVE AMINO ACID PROFILES BY U.S. MANUFACTURERS

| | TRA-VA-SOL 8.5% | TRA-VA-SOL 10% | BAN-CHA MIN 4% | TRA-VA-SOL 0.5% WITH 4% BCAA (1) | TRA-VA-SOL 10% WITH 4% BCAA (2) | TRA-VA-SOL 8.5% WITH 4% BCAA (3) | TRA-VA-SOL 10% WITH 4% BCAA (4) | REM-A-MIN 6.5% | FRE-A-MIN 8.5% | FRE-A-MINE 10% | FRE-A-MINE HBC | FRE-A-MINE HCC | NEPH-RA-MINE 5.4% | HEP-TA-MINE 8% | PRO-CALA-MINE | AMINO-SYN 8.5% | AMINO-SYN 10% | AMINO-SYN RF |
|---|---|---|---|---|---|---|---|---|---|---|---|---|---|---|---|---|---|---|
| ESSENTIAL AMINO ACIDS (mg/100 ml) | | | | | | | | | | | | | | | | | | |
| LEUCINE | 526.00 | 730.00 | 1380.00 | 1095.33 | 1163.33 | 953.00 | 1055.00 | 600.00 | 770.00 | 910.00 | 1870.00 | 1370.00 | 980.00 | 1100.00 | 270.00 | 810.00 | 940.00 | 726.00 |
| ISOLEUCINE | 406.00 | 600.00 | 1380.00 | 1055.33 | 1120.00 | 893.00 | 990.00 | 500.00 | 590.00 | 690.00 | 760.00 | 760.00 | 560.00 | 900.00 | 210.00 | 620.00 | 720.00 | 462.00 |
| VALINE | 390.00 | 580.00 | 1240.00 | 956.67 | 1020.00 | 815.00 | 910.00 | 820.00 | 560.00 | 660.00 | 880.00 | 880.00 | 640.00 | 840.00 | 200.00 | 680.00 | 800.00 | 528.00 |
| PHENYLALANINE | 526.00 | 560.00 | 0.00 | 175.33 | 186.67 | 263.00 | 280.00 | 490.00 | 480.00 | 560.00 | 320.00 | 320.00 | 880.00 | 100.00 | 170.00 | 380.00 | 440.00 | 726.00 |
| METHIONINE | 492.00 | 400.00 | 0.00 | 164.00 | 193.33 | 246.00 | 200.00 | 400.00 | 450.00 | 530.00 | 250.00 | 250.00 | 880.00 | 100.00 | 160.00 | 340.00 | 400.00 | 726.00 |
| LYSINE | 492.00 | 580.00 | 0.00 | 164.00 | 193.33 | 246.00 | 290.00 | 500.00 | 620.00 | 750.00 | 410.00 | 410.00 | 640.00 | 610.00 | 220.00 | 624.00 | 720.00 | 535.00 |
| HISTIDINE | 372.00 | 480.00 | 0.00 | 124.00 | 160.00 | 186.00 | 240.00 | 450.00 | 240.00 | 280.00 | 160.00 | 160.00 | 250.00 | 240.00 | 85.00 | 260.00 | 300.00 | 429.00 |
| THREONINE | 356.00 | 420.00 | 0.00 | 118.67 | 140.00 | 178.00 | 210.00 | 420.00 | 340.00 | 400.00 | 200.00 | 200.00 | 400.00 | 450.00 | 120.00 | 460.00 | 520.00 | 330.00 |
| TRYPTOPHAN | 152.00 | 180.00 | 0.00 | 50.67 | 60.00 | 76.00 | 90.00 | 380.00 | 130.00 | 150.00 | 90.00 | 90.00 | 200.00 | 66.00 | 46.00 | 150.00 | 160.00 | 165.00 |
| NON-ESSENTIAL AMINO ACIDS (mg/100 ml) | | | | | | | | | | | | | | | | | | |
| ALANINE | 1760.00 | 2070.00 | 0.00 | 586.67 | 690.00 | 880.00 | 1035.00 | 560.00 | 600.00 | 710.00 | 400.00 | 400.00 | 0.00 | 770.00 | 210.00 | 1100.00 | 1200.00 | 0.00 |
| GLYCINE | 1760.00 | 1030.00 | 0.00 | 586.67 | 343.33 | 880.00 | 515.00 | 300.00 | 1190.00 | 1408.00 | 330.00 | 330.00 | 0.00 | 900.00 | 420.00 | 1100.00 | 1280.00 | 0.00 |
| ARGININE | 880.00 | 1150.00 | 0.00 | 293.38 | 383.38 | 440.00 | 575.00 | 630.00 | 810.00 | 950.00 | 580.00 | 580.00 | 0.00 | 600.00 | 290.00 | 850.00 | 980.00 | 600.00 |
| PROLINE | 856.00 | 680.00 | 0.00 | 118.67 | 226.67 | 178.00 | 340.00 | 350.00 | 1120.00 | 630.00 | 630.00 | 630.00 | 0.00 | 800.00 | 340.00 | 750.00 | 860.00 | 0.00 |
| TYROSINE | 34.00 | 40.00 | 0.00 | 11.33 | 13.33 | 17.00 | 20.00 | 40.00 | 20.00 | 0.00 | 0.00 | 0.00 | 0.00 | 0.00 | 180.00 | 44.00 | 44.00 | 0.00 |
| SERINE | 0.00 | 500.00 | 0.00 | 0.00 | 166.67 | 0.00 | 250.00 | 300.00 | 500.00 | 590.00 | 330.00 | 330.00 | 0.00 | 500.00 | 20.00 | 370.00 | 428.00 | 0.00 |
| CYSTEINE | 0.00 | 0.00 | 0.00 | 0.00 | 0.00 | 0.00 | 0.00 | 0.00 | 20.00 | 20.00 | 20.00 | 20.00 | 0.00 | 20.00 | 2.94 | 0.00 | 0.00 | 0.00 |
| AMINO ACIDS AS % | 8.50 | 10.00 | 4.00 | 5.50 | 6.00 | 6.25 | 7.00 | 6.50 | 8.42 | 9.23 | 6.73 | 6.73 | 3.35 | 8.00 | 2.94 | 8.54 | 9.86 | 5.23 |
| BCAA (g/100 ml) | 1.32 | 1.91 | 4.00 | 3.11 | 3.30 | 2.66 | 2.96 | 1.92 | 1.92 | 2.26 | 3.01 | 3.01 | 2.08 | 2.84 | 0.68 | 2.11 | 2.46 | 1.72 |
| BCAA % | 15.55 | 19.10 | 100.00 | 56.49 | 55.06 | 42.57 | 42.21 | 29.54 | 22.80 | 24.49 | 44.73 | 44.73 | 38.08 | 35.52 | 23.12 | 24.71 | 24.94 | 32.83 |
| EAA % | 37.12 | 43.30 | 100.00 | 39.04 | 41.77 | 38.56 | 42.65 | 43.20 | 41.80 | 49.30 | 44.40 | 44.40 | 53.30 | 44.06 | 14.81 | 43.24 | 50.00 | 46.27 |
| BCAA:AAA Ratio | 1.0:0.539 | 1.0:0.408 | N/A | 1.0:0.076 | 1.0:0.079 | 1.0:0.134 | 1.0:0.132 | 1.0:0.359 | 1.0:0.318 | 1.0:0.314 | 1.0:0.136 | 1.0:0.136 | 1.0:0.519 | 1.0:0.058 | 1.0:0.318 | 1.0:0.272 | 1.0:0.262 | 1.0:0.519 |
| Manufacturer | Travenol | Travenol | Travenol | Travenol | Travenol | Travenol | Travenol | Trav-enol | Amer. McGaw | Amer. McGaw | Amer. Mc-Gaw | Amer. Mc-Gaw | Amer. McGaw | Amer. McGaw | Amer. McGaw | Abbott | Abbott | Abbott |

FOOTNOTES
(1) 2 VOLUMES OF 4% BRANCHAMIN TO 1 VOLUME 8.5! TRAVASOL
(2) 2 VOLUMES OF 4% BRANCHAMIN TO 1 VOLUME 10% TRAVASOL
(3) 1:1 RATIO 4% BRACHEMIN TO 8.5% TRAVASOL
(4) 1:1 RATIO 4% BRACHIAMIN TO 10% TRAVASOL

Studies have shown that the polyamine biosynthetic pathways may be important in the development of amino acid solutions specific for cancer patients. An important consideration is the interaction between tumor polyamine production and a specific amino acid solution that may enhance RBC polyamines as tumor markers. It has been determined that administration of TPM solutions to patients with occult malignancies produce changes in polyamine levels compared with noncancer patients while plasma CEA and creatine kinase-brain band levels did not change, indicating a specific increase in polyamine levels in tumor-bearing patients. Accordingly, the sensitivity and specificity of RBC polyamine measurements to detect occult disease may be enhanced with new amino acid solutions which include substrates for tumor polyamine production such as ornithine or arginine.

In recent years, chemotherapeutic agents that directly inhibit polyamine synthesis have been developed. Difluoromethylornithine (DFMO), one such drug, is an irreversible inhibitor of ODC and potentially can be given continuously with significant anti-tumor effects. This drug is relatively non-toxic to the host while producing inhibition of putrescine synthesis in tumors. Studies in a rat-tumor model demonstrate that DMFO infusion can produce a 90% decrease in tumor putrescine levels without suppressing peripheral platelet counts.

Although DFMO can effectively block tumor putrescine biosynthesis, the resultant antitumor effect is cytostasis and not cytotoxicity. For example, DFMO reduces the growth rate of an MCA sarcoma but does not produce tumor regression. This finding is consistent with reports of other investigators who showed that DFMO is a cytostatic agent. However, studies indicate that a significant role exists for DFMO agents, permitting the future development of combination chemotherapeutic regimens which incorporate DFMO.

Although the toxicity associated with DFMO therapy are not, in general, as severe as other types of chemotherapy, in limited clinical trials it has been found to promote a dose-related thrombocytopenia. Moreover, studies in rats have shown that continuous infusion of DFMO for 12 days significantly reduces platelet counts compared with controls. Other investigations have made similar observations in which thrombocytopenia is the major toxicity of continuous i.v. DFMO therapy. These findings suggest that DFMO may significantly inhibit ODC activity of the bone marrow precursors of megakaryocytes. It is contemplated by the present inventors that the formulations disclosed herein, in addition to promoting tumor polyamine production for diagnostic purposes, constitute specific antidotes to ODC-directed chemotherapy.

One means to reverse DFMO toxicity in the host is to infuse amino acid precursors of polyamine biosynthesis. Special amino acid solutions rich in ornithine or arginine made in accordance with the present invention can rescue the bone marrow from the toxic side effects of DFMO. For example, the addition of ornithine to feeder solutions in a rat-tumor model resulted in a significant reversal in the platelet suppression. Additionally, the constant infusion DFMO technology in a rat-tumor model permits the ability to test such new amino acid solutions in reducing DFMO induced thrombocytopenia. It is hypothesized that such solutions provide substrates which stimulate the production of polyamines in normal cells which are sensitive to ODC-directed chemotherapy, thus promoting recovery from toxic side effects of the drugs. Similarly, it is hypothesized that solutions containing polyamine precursors may serve to enhance ODC-directed chemotherapy against certain tumors, as adjuvants to radiation therapy or may in themselves exhibit anti-tumor activity against some tumors.

Solutions prepared with essential amino acids + ornithine produce higher RBC putrescine levels compared with essential amino acids or essential amino acids + arginine. RBC and tumor spermidine and spermine levels are not affected to as great an extent by these solutions. The specific increases in putrescine levels may be explained by the proximity of certain amino acid components to the pathways of polyamine synthesis. Use of these new amino acid solutions could be important to detect occult malignancy following surgical resection. For example, colorectal carcinoma patients represent an ideal population to test the tumor-detecting capabilities of RBC polyamine levels enhanced by amino acid solutions. Such detection studies could be done, for example, two to three months postoperatively.

Use of a new amino acid solution to enhance the cancer detecting properties of blood polyamine measurements represents an improvement of currently available diagnostic methods. Breast and colorectal cancers represent possible malignancies where this may be applicable. Pathologic assessment of axillary lymph node involvement is the only means to predict risk of future metastatic disease in women with either clinical stage I or II disease. By increasing our ability to select patients with positive lymph node involvement, the benefits of adjuvant chemotherapy will be increased. Similar application can be made for patients with Dukes $B_2$ or $C_2$ rectal carcinomas. CEA measurements or diagnostic radiologic tests are not effective for selecting those patients with microscopic residual disease that can be treated by postoperative radiotherapy to the pelvis. Amino acid solutions with a novel amino acid such as ornithine could enhance polyamine detection of residual disease and, thereby, select patients who would benefit the most from postoperative adjuvant radiotherapy.

Enhanced cancer detection with polyamine measurements after TPN administration potentially represents considerable improvement over other tumor markers. Infusion of amino acid solutions rich in ornithine increase tumor polyamine production, thus elevating their levels in peripheral blood. Infusion of arginine or ornithine alone, that is, not in combination with one or all of the essential amino acids, has not produced elevated blood polyamine levels in experimental tumor system.

b. Determination of Polyamine Levels

Numerous techniques are known in the art for determining polyamine levels in aqueous biological samples such as urine and plasma. Generally, such techniques involve subjecting the aqueous sample to amino acid analysis by an automated amino acid analysis. In this manner, individual determinations of putrescine, spermidine and spermine may be made. More recently, enzymatic methods have been developed as disclosed in Japanese patent Nos. 8402700 and 8482099.

Although urine and plasma may be utilized for polyamine determinations in accordance with the present invention, it has been determined by the present inventors that red blood cell polyamine levels more accurately reflect tumor-related increases in polyamine production. Therefore, determination of RBC polyamines is a preferred method where accuracy is required, although this procedure is somewhat more involved. The following method is a representative RBC polyamine level determination.

After obtaining the blood sample by venipuncture, or some other suitable means, blood hematocrit is determined and the blood is centrifuged for 10 minutes at 500 g. The plasma is removed for albumin determination and the remaining cells are washed with an equal volume of cold 0.9% NaCl and centrifuged at 200 g for 15 minutes. The buffy coat is then carefully aspirated along with the supernatant and discarded. After thoroughly mixing the packed RBC, a 1.0 ml aliquot is extracted for polyamine analysis. While shaking continuously with a Vortex mixer, 2.5 ml of freshly prepared 6% trichloroacetic acid (TCA) is added followed by 60 ul of 100% TCA. This is done to avoid insufficient mixing if 100% TCA is added directly to RBC. The samples are mixed thoroughly for a minimum of 3 minutes and frozen at −70° C. if further extraction steps are performed. The samples are thawed and centrifuged at 200×g for 15 minutes. The supernatant is then transferred to tubes containing 40 ul of concentrated HCl. The samples are washed twice with anhydrous ether and dried. The pellets are dissolved in 100 ul of 0.5 N HCl and centrifuged at 200 g. The clear supernatant is then analyzed for polyamines using, for example, a Durrum D-500 amino acid analyzer.

In an additional embodiment, the patient's RBC polyamine level is determined both before and after administration of amino acid solutions. This allows the physician to both identify the "reactivity" of the patient's polyamine level and to further compare with normal profiles. The following example demonstrates the use of total parenteral nutrition solutions to detect recurrent malignant disease.

EXAMPLE I

DETECTION OF RECURRENT MALIGNANT DISEASE BY POLYAMINE ANALYSIS IN PATIENTS RECEIVING TOTAL PARENTERAL NUTRITION

This study was performed to demonstrate that total parenteral nutrition (TPN) results in significant increases in erythrocyte (RBC) polyamine levels in patients with clinically occult recurrent malignant disease. TPN was administered preoperatively to six noncancer patients and seven patients who had a history of curative operation for malignant disease and, after receiving TPN, were found to have recurrent disease. RBC putrescine (PUT), spermidine (SPD), and spermine (SPM) were determined before and after preoperative TPN in each patient. Plasma carcinoembryonic antigen (CEA) and creatine kinase brain band (CK-BB) were also measured during the study as controls. Mean length ($\pm$S.E.) of preoperative TPN for the noncancer group and the group harboring occult recurrent disease was $8.4\pm2.9$ days and $9.6\pm3.6$ days, respectively, There were no significant changes in RBC polyamine and plasma CEA and CK-BB levels in the noncancer group after TPN. Those patients with occult malignant disease had significant increases in RBC PUT and PUT/SPD ratio (p 0.05) during TPN, while RBC SPD and SPM and plasma CEA and CK-BB did not change. The data indicates that short-term TPN can enhance the use of polyamine measurements as markers of recurrent malignant disease.

PATIENT POPULATION

Patients who required preoperative TPN in order to restore or prevent nutritional deficits before an operative procedure were entered into this study. Patients who received chemotherapy or radiation therapy or underwent an operative procedure within three months of this study were excluded. Women with active ovulatory cycles were also excluded. The only treatment given during preoperative TPN was nutritional therapy. All patients had normal renal function (plasma creatinine less than 1.4 mg/dL and BUN values less than 25 mg/dL) and normal liver function (serum bilirubin less than 1.4 mg/dL) as prerequisites for entry into the study. This study was conducted with the approval of the Human Surveillance Committee of M.D. Anderson Hospital and the informed consent of the patient.

There were six patients who required preoperative TPN and who were free of malignant disease, as documented by exploratory laparotomy, histologic evaluation of the respected specimens, and length of disease-free status (greater than five years). There were seven patients with clinically occult recurrent malignant disease during their course of preoperative TPN. These patients had had either a "curative" operative procedure or had a suspicious lesion that could not be proven as recurrent malignant disease by diagnostic evaluation, which included roentgenographic and endoscopic studies. Disease status was determined by exploratory laparotomy following preoperative TPN or by follow-up clinic visits.

NUTRITIONAL REGIMEN

TPN solutions consisted of 50% glucose (500 ml), 10% crystalline amino acids (500 ml), NaCl (40–60 mEq/L), KCl (20–40 mEq/L), $KH_2PO_4$ (10–15 mEq/L), Ca gluconate (4.5 mEq/L), $MgSO_4$ (10–15 mEq/L), MVI-12 (10 ml), and trace elements (2 ml). A 10% soybean oil emulsion (500 ml) was administered biweekly. TPN solutions were administered continuously through a central venous catheter at a rate of 30–50 calories/kg body weight/day and 2.0–3.0 g amino acid/kg body weight/day. Fluid and electrolyte balance was monitored every Monday, Wednesday, and Friday.

STUDY DESIGN

Each patient was hospitalized for 7 to 10 days of preoperative TPN. Before TPN was started, venous blood (7 ml in a heparin-coated tube) was obtained. After completion of preoperative TPN and on the day before the operative procedure, a second venous blood sample was obtained. RBC polyamine determinations and plasma CEA and CKBB measurements were done before and after preoperative TPN for each patient. In this manner, each patient served as his or her own control in determining the effect of TPN on RBC polyamines and plasma CEA and CK-BB levels. Analysis of data was done by a paired Student's t-test, comparing levels before and after TPN within the noncancer and cancer groups.

POLYAMINE, CEA AND CK-BB DETERMINATIONS

RBC putrescine, spermidine, and spermine levels were measured by high performance liquid chromatography using a Durrum D-500 amino acid analyzer, (Dionex Corp., Palo Alto, Calif.) as described above. Plasma CEA was determined by an enzyme immunoassay procedure kit (Abbott Laboratories, North Chicago, Ill.) and plasma CK-BB was measured with a radioimmunoassay method (Mallinkrodt, Inc., St. Louis, Mo.).

The clinical history of each patient is shown in Table II. The six noncancer patients received preoperative TPN for 8.4±2.9 days (mean±S.E.). Patients #4 and #5 were both studied twice, six and twelve months apart, because of two separate episodes of weight loss induced by short gut syndrome. This accounts for the eight determinations of sequential polyamine measurements for this group. There were seven patients with clinically occult malignant disease. Three patients had recurrent disease at laparotomy immediately following preoperative TPN. The other four patients developed recurrent disease at three months to two years after the study. The mean length of TPN for this group was 9.6±3.6 days. Mean weight loss, based on usual body weight, was 7.1±1.1% TPN was started. Preoperative TPN was given without infectious or metabolic complications.

TABLE II

| Patient Population | | |
|---|---|---|
| Age | Sex | Diagnosis |
| Patients with Occult Malignant Disease | | |
| 59 | F | Recurrent bladder carcinoma 9 mos. after TPN |
| 58 | F | Recurrent esophageal carcinoma 3 mos. after TPN |
| 49 | M | Recurrent pancreatic carcinoma 7 mos. after TPN |
| 60 | M | Recurrent esophageal carcinoma discovered at laparotomy |
| 40 | M | Recurrent esophageal carcinoma discovered at laparotomy |
| 48 | F | Gastric carcinoma discovered at laparotomy |
| 78 | F | Recurrent colon carcinoma 24 mos. after TPN |
| Patients with Benign Disorders | | |
| 50 | F | Benign esophageal stricture |
| 55 | F | Benign gastric ulcer |
| 30 | F | Pseudointestinal obstruction |
| 20 | F | Chronic radiation enteritis and short gut syndrome* |
| 51 | M | Chronic radiation enteritis and short gut syndrome* |
| 71 | F | Benign gastric ulcer |

*patients were studied twice for a total of eight sequential polyamine studies for the noncancer group.

Polyamines could not be detected in TPN solutions. Changes in RBC count (x$10^6$/mm$^3$) were similar for both groups with a mean decrease of 4.3% during TPN. FIG. 1 shows the changes in RBC putrescine, spermidine, and spermine for both groups. Eight determinations in six noncancer patients showed no significant increases in RBC polyamine levels during TPN. The patients with clinically occult malignant disease had a significant increase in RBC putrescine levels ($p<0.01$), while RBC spermine levels increased but not significantly. There was a trend toward higher, but not significant, spermidine levels in this group ($p<0.07$).

Changes in RBC putrescine: spermidine and spermidine: spermine ratios during TPN for both groups are shown in FIG. 3. The spermidine: spermine ratio did not change for either group. The patients with clinically occult malignant disease had a significant increase in the putrescine: spermidine ration, while the noncancer group did not. Plasma CEA and CK-BB levels did not increase significantly during TPN in either group of patients as shown in Table III.

TABLE III

| Plasma CEA and CKBB Data During TPN[a] | | | | | |
|---|---|---|---|---|---|
| | | Plasma CEA (ng/ml)[b] | | Plasma CKBB (ng/ml)[b] | |
| | n | Pre | Post | Pre | Post |
| Noncancer | 6 | 2.9 ± 1.6 | 2.8 ± 1.4 | 3.6 ± 2.1 | 3.5 ± 2.4 |
| Occult Cancer | 4 | 2.4 ± 2.0 | 5.0 ± 4.9 | 1.9 ± 0.5 | 1.6 ± 0.3 |

[a]Plasma carcinomembryonic antigen (CEA) and creatine kinase brain band (CKBB) were determined before (Pre) and after (Post) preoperative TPN in noncancer patients and patients with clinically occult malignant disease. Normal values for CEA are 0–3 ng/ml (non-smokers) and 0–6 ng/ml (Smokers).
[b]Values represent ± SD The previous example demonstrates that two procedures may enhance the value of polyamines as markers of recurrent malignant disease. First, using each patient as his or her own control, polyamine measurements were determined at two different time points. Second, in between the two measurements, a hypertonic glucose-amino acid solution was infused. The combination of these two procedures seemed to enhance the detection of malignant disease with polyamine measurements.

Increases in RBC putrescine during TPN are thus related to either increased substrate levels with constant tumor ODC activity or increased tumor ODC activity and subsequent proliferation. In addition it appears that increases in RBC polyamines during TPN in cancer patients are related to tumor proliferation.

An important concept of polyamine metabolism is that tumors may have a greater requirement for polyamine synthesis, whereas normal tissues may have a lesser requirement for polyamines because of their controlled growth behavior. By providing nutrient substrates, TPN may be increasing polyamine production in tumor cells that then excrete these products into the extracellular space and are absorbed by RBC.

In particular, the TPN solution utilized in the previous example was Travasol 10%, whose amino acid composition is displayed above in Table I. Travasol 10% is used in compounding a feeding solution for general administration in patients with benign or malignant diseases. However, the present inventors contemplate that any of the commercially available parenteral amino acid formulations will function in the practice of the present invention. In fact, amino acid formulations may be designed which include a wide range of amino acid concentrations and combinations. For example, parenteral solutions with up to three times the amino acid concentration of commercial TPN solutions would not be considered toxic and would therefore be functional in the present invention. It appears that the only requirement for practicing the present invention is that such solutions contain one or more of the essential amino acids and either ornithine or arginine, or both, with ornithine being preferred.

EXAMPLE II

FEEDING SOLUTIONS CONTAINING ORNITHINE

Ornithine has been combined with essential amino acids and utilized in a rat tumor model to demonstrate its potential utility in man. Rats having been implanted with a methylcholanthrene (MCA) - induced tumors received continuous infusion of one-fold diluted Nephramine 5.4% in combination with either arginine or ornithine. Polyamine levels were determined both before and after feeder solutions infusion in control no arginine or ornithine experimental (tumor-bearing rats given solutions with ornithine or arginine) and sham or chow-fed rats.

Male Fisher 344 rats were purchased from Timco Harlan-Sprague-Dawley (Houston, Tex.). All rats were allowed a 7-day acclimation period with chow (Purina 5001) and water ad libitum. A methylcholanthrene-induced fibrosarcoma (0.17 g) was implanted as a brei into the right flank under anesthesia and the animals were fed a chow diet for 21 days. When the tumors were at least 1.0 cm in width, two-dimensional measurements with calipers were instituted and the equation, length (cm)×(width [cm])$^2$×½ = grams of tumor tissue, was used to estimate tumor weight. When tumor weight reached 14±3 g (21 days of chow diet), the animals were randomized into three groups by tumor weight and under anesthesia a Silastic central venous catheter was placed in the superior vena cava through an internal jugular vein cutdown. The animals were then allowed to recover overnight and continuous infusions were started the next morning. Essential amino acids-+arginine rats (E+A rats) received a continuous infusion of 500 ml 60% glucose+500 ml 5.4% Nephramine with 0.58 g/100 ml or arginine added for 6 days. Essential amino acids+ornithine rats (E+O rats) received 500 ml 60% glucose+500 ml 5.4% Nephramine with 0.44 g/100 ml of ornithine added. The ornithine and arginine were added at equimolar concentrations. Nephramine is a parenteral amino acid solution consisting of eight essential amino acids and histidine. After 6 days of continuous infusion, the animals were sacrificed by aortic bleeding. Liver and tumor were excised and weighed and kept frozen at −70° C. until assays were done. Only viable, nonnecrotic tumor tissue was saved and assayed.

Preparation of tumor tissue for polyamine assay was done in the following manner. Tumor tissue weighing 0.5 to 1.5 g was cut into small pieces and put into a disposable tube (16×100 mm). Ice-cold 4% sulfosalicylic acid was then added at 2 ml/g wet tissue. This mixture was homogenized in an ice bath for 40 seconds using the Brinkman Polytron homogenizer (P10ST generator set at 8.5). The suspension was centrifuged at 100,000 g for 30 minutes and the resulting clear supernatant was analyzed for polyamines on a Durrum D-500 amino acid analyzer.

Statistical analyses were done with Student's t test (one tail). RBC determinations were performed as described above; blood was obtained by aortic puncture.

The results are demonstrated in Table IV. As Table IV indicates, levels of putrescine within the tumors were increased approximately three fold whereas levels of all three polyamines were significantly increased in the rat's RBC's. In both cases, ornithine functioned better than arginine, but both appeared to promote an increase in tumor-related levels. Comparison of these values from tumor-bearing rats to non-tumor bearing would demonstrate an even more substantial difference in relative polyamine levels.

TABLE IV

| Nutritional Regimen[1] | n | Tumor Weight[1] Initial | Final | % Change[2] |
|---|---|---|---|---|
| Chow | 5 | 13.3 ± 2.6 | 32.9 ± 5.3 | 134 ± 32 |
| E | 4 | 14.0 ± 2.8 | 35.7 ± 6.9 | 135 ± 42 |
| E + A | 6 | 10.5 ± 2.2 | 25.7 ± 3.4 | 153 ± 68 |
| E + O | 7 | 11.1 ± 2.2 | 24.4 ± 4.9 | 123 ± 34 |

| Tissue | Nutritional Regimen | n | Polyamine Levels Putrescine | Spermidine | Spermine |
|---|---|---|---|---|---|
| Erythrocyte | Chow | 5 | 0.91 ± 0.21 | 71 ± 57 | 6.1 ± 4.1 |
| | E | 4 | 1.42 ± 0.32 | NA | NA |
| | E + A | 6 | 1.60 ± 0.52 | 69 ± 45 | 6.5 ± 2.6 |
| | E + O | 7 | 1.85 ± 0.36 | 125 ± 9 | 10.9 ± 3.3 |
| Tumor | Chow | 5 | 46.9 ± 12.2 | 797 ± 80 | 392 ± 21 |
| | E | 4 | 22.9 ± 4.4 | 901 ± 39 | 480 ± 35 |
| | E + A | 6 | 50.5 ± 13.3 | 871 ± 69 | 409 ± 36 |
| | E + O | 7 | 73.6 ± 17.1 | 919 ± 90 | 415 ± 30 |

[1]Fibrosarcoma, growing s.c.
[2]% increase in tumor weight.

Additionally, the previous example demonstrates that 450 mg of ornithine for every 100 ml of the amino acid formulation functions satisfactorily and continuous infusion of such solutions which posed no toxicity problems. It is contemplated that amino acid solutions ranging from 50 mg up to 2 g per 100 ml of solutions (with between 50 and 750 mg/100 ml being a preferred range for arginine and ornithine) should function satisfactorily without loss of appreciable activity or increased toxicity. However, for the detection of microscopic tumors and as an antidote to ODC-directed antitumor therapy, higher concentrations of ornithine are suggested.

Another experiment which utilized formulations containing amino acid precursors of RBC polyamines, compared the response of tumor-bearing rats (TB) to non tumor-bearing rats (NTB). The study was performed basically in the manner described above with the following indicated differences. Fibrosarcoma-bearing (TB) and non-tumor being F344 rats (NTB) were infused with either a typical feeding solution (30% glucose+5% essential amino acids), with essential amino acids (19 g/L, 30% glucose) plus arginine at 19.5% g/l (E+A). Chow rats (C) were fed chow with no i.v. infusion.

TABLE V

| Treatment | N | NTB PUT | N | WT. | PUT | N | TB WT | PUT |
|---|---|---|---|---|---|---|---|---|
| C | 13 | .39 ± .10 | 5 | 13 ± 3 | .7 ± 10 | 6 | 37 ± 10 | 1.2 ± 0.2 |
| E | 9 | .41 ± .07 | 6 | 15 ± 2 | .9 ± .3 | 4 | 36 ± 7 | 1.4 ± 0.3 |
| E + A | 5 | .62 ± .22 | 8 | 11 ± 3 | 1.9 ± .3 | 2 | 51 ± 22 | 5.0 ± 2.7 |

Where N is the number of rats included in the study, PUT is RBC levels (nm/g/ml, means ± SD) of putrescine determined by HPLC.

As demonstrated in Table V, the increase in RBC putrescine levels in NTB rats following administration of feeding solutions which included a specific putrescine precursor (arginine) was significantly greater ($p<0.05$) than those receiving chow or essential amino acids only. However, the RBC putrescine level of TB rats receiving E+A was significantly greater than any other group in the study. It should also be noted that increased putrescine levels were found to be proportional to tumor weight.

c. Reduction of DFMO Induced Thrombocytopenia

Animal and clinical studies have shown that the major host toxicity associated with the continuous infusion of DFMO is thrombocytopenia (Ota et al. (1986), Int. J. Cancer, 38:245; see also FIG. 3 herein). In the above described rat model, a continuous infusion of DFMO was given through a central venous catheter. Non-tumor-bearing and tumor-bearing rats received continuous i.v. DFMO for 12 days. The DFMO doses typically employed were 500 mg, 1000 mg, and 2000 mg per kg body wt per day. Although there was histological evidence of small intestinal mucosal atrophy at these doses, no significant clinical toxicity was seen during the 12 day study. However, dose related thyrombocytopenia was observed, as shown in FIG. 3. White cell count and hematocrit changes were not significantly altered by DFMO administration.

Figure 4:
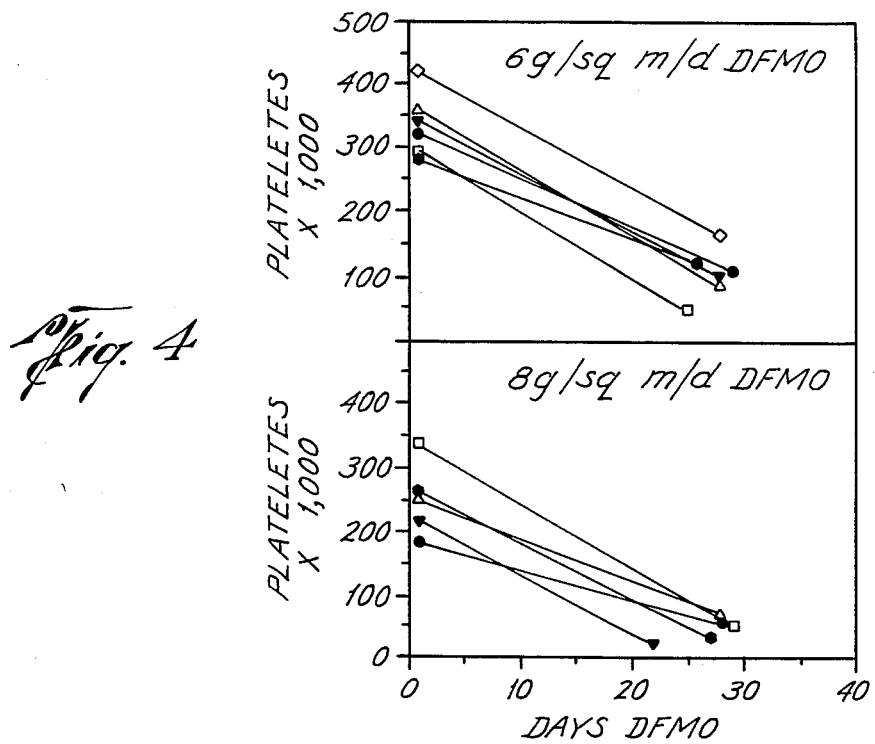
FIG. 4. Platelet counts plotted against days of continuous i.v. DFMO infusion in patients with advanced colorectal carcinoma. The upper graph shows the platelet suppression at 6 g DFMO/sq m/d. The lower graph depicts the platelet suppression at 8 g DFMO/sq m/d. Each course of infusion is shown by two points representing day 1 of infusion and day 22 to 28 when DFMO was discontinued. The paired points are connected by a straight line. The data show that platelet suppression is the major limiting host toxicity of DFMO given as a continuous infusion. The simultaneous infusion of ornithine with DMFO may inhibit platelet toxicity.

Clinical studies with patients undergoing DFMO therapy have shown that the continuous infusion of DFMO for 28 days also produced significant clinical thrombocytopenina. Eleven cycles of 28 day DFMO infusion have been administered to 7 patients at doses of either 6 or 8 g DFMO/m$^2$/day. As shown in FIG. 4, the platelet suppression was significant at both doses. There was significantly greater platelet at the 8 g dose as compared with the 6 g dose. Significant suppression of the hematocrit was also noted with a trend toward dose related suppression. White cell count was not affected by either dose. There was no incidence of nausea, vomiting or diarrhea. There were two patients who experienced decreased hearing acuity at 8 h DFMO/m$^2$/day. All toxicities resolved spontaneously within two weeks of discontinuing the DFMO infusion.

The following study was designed to determine if the simultaneous administration of ornithine with DFMO would reduce thrombocytopenia. Central venous catheters were inserted into Fisher 344 male rats. The animals received approximately 1500 mg DFMO per kg body wt per day as a contiuous i.v. infusion. Ornithine HCl (Ajinomoto, Ltd., New York, N.Y.) was added to the saline solutions at a final concentration of 3.3 mmol/100 ml. This concentration is equimolar to the arginine concentration in 10% Travasol. After 12 days of infusion the rats were sacrificed and platelet counts were determined in peripheral blood.

Table VI shows the results of this experiment. There were 3 treatment groups consisting of saline, DFMO and DFMO with ornithine. As shown in Table VI, the simultaneous administration of ornithine with DFMO blocked platelet suppression. DFMO alone resulted in a significant decrease in platelet count as compared with the saline treatment.

TABLE VI

Influence of Ornithine Co-administration On DFMO-Induced Thrombocytopenia in the Rat

| Treatment | n | Platelets ($\times 10^3$/cu. mm) |
|---|---|---|
| Saline | 3 | 780 ± 253 |
| DFMO[b] | 5 | 409 ± 127 |
| DFMO + Orn[c] | 6 | 958 ± 195[d] |

[a]Fischer 344 male rats received a continuous infusion of saline, DFMO + ornithine for 12 days. All rats received chow and water ad libitum.
[b]DFMO dose = 1444 ± 73 mg/kg/d.
[c]DFMO dose = 1429 ± 85 mg/kg/d; Ornithine dose = 436 mg/100 ml or 3.3 mmoles/100 ml infusion.
[d]Mean differs significantly compared with DFMO treated rats.

These results demonstrated that parenteral administration of polyamine precursors can significantly reduce DFMO induced platelet toxicity. The results further indicate that, at least in the animal system studied, a concentration of approximately 33 mM is adequate to prevent or reduce the occurrence of thrombocytopenia. However, it is contemplated that virtually any non-toxic amount of polyamine precursor can be employed. Moreover, the results indicate that polyamine precursors may be administered alone and do not require the presence of additional amino acids.

Those of skill in the art will recognize that, although the present invention is disclosed in terms of specific embodiments, one may depart from such embodiments and still remain within the scope of the invention. All such departures are considered to be within the scope of the pending claims.

What is claimed is:

1. A method for reducing difluoromethylornithine associated toxicity in a patient comprising administering to a patient in need thereof a parenteral formulation comprising from about 0.05 about 2.0 grams per 100 ml. of at least one essential amino acid selected from the group consisting of leucine, isoleucine, valine, phenylalanine, lysine, histidine, threonine, and tryptophan; in combination with from about 50 to about 750 mg per 100 ml. of a polyamine precursor selected from the group consisting of methionine, arginine, and ornithine.

2. The method of claim 1, wherein the pharmacologically acceptable amount of the selected essential amino acid comprises the following weight range of the amino acid for every 100 milliliters of the formulation:

250 to 1400 mg of leucine;
200 to 1400 mg of isoleucine;
200 to 1250 mg of valine;
100 to 900 mg of phenylalanine;
150 to 750 mg of lysine;
85 to 500 mg of histidine;
100 to 550 mg of threonine; and
50 to 200 mg of tryptophan.

3. A method for reducing difluoromethylornithine associated toxicity in a patient comprising administering to patient in need thereof a parenteral formulation comprising a therapeutically effective amount of a polyamine precursor selected from the group consisting of methionine, arginine, and ornithine.

4. The method of claim 3 wherein the formulation further comprises a total parenteral nutrition solution comprising essential amino acids.

5. The method of claim 3 wherein the therapeutically effective amount of the polyamine precursor is between 50 and 750 mg for every 100 milliliters of the formulation.

6. The method of claim 1 or 3 wherein the selected polyamine precursor is methionine.

7. The method of claim 1 or 3 wherein the selected polyamine precursor is ornithine.

8. The method of claim 7 wherein the ornithine is present in the formulation at a concentration of approximately 33 mM.

9. The method of claim 1 or 3 wherein the selected polyamine precursor is aginine.

* * * * *

UNITED STATES PATENT AND TRADEMARK OFFICE
CERTIFICATE OF CORRECTION

PATENT NO. : 4,859,452
DATED : August 22, 1989
INVENTOR(S) : Jaffer Ajani et al

It is certified that error appears in the above-identified patent and that said Letters Patent is hereby corrected as shown below:

At column 16, line 61, please delete "aginine" and insert therefor --arginine--.

Signed and Sealed this

Third Day of July, 1990

Attest:

HARRY F. MANBECK, JR.

*Attesting Officer*  *Commissioner of Patents and Trademarks*